(12) United States Patent
Molock et al.

(10) Patent No.: US 6,531,432 B2
(45) Date of Patent: Mar. 11, 2003

(54) CONTACT LENS PACKAGING SOLUTIONS

(75) Inventors: Frank F. Molock, Orange Park, FL (US); James D. Ford, Orange Park, FL (US); Annie C. Maiden, Jacksonville, FL (US); Robert N. Love, La Sal, UT (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 09/731,553

(22) Filed: Dec. 7, 2000

(65) Prior Publication Data

US 2002/0071789 A1 Jun. 13, 2002

(51) Int. Cl.7 .................................................. C11D 1/66
(52) U.S. Cl. ........................ 510/112; 510/421; 510/503; 510/506; 206/5.1
(58) Field of Search ................................ 510/112, 421, 510/503, 506; 206/5.1

(56) References Cited

U.S. PATENT DOCUMENTS

| | | | |
|---|---|---|---|
| 3,882,036 A | | 5/1975 | Krezanoski et al. |
| 3,954,644 A | * | 5/1976 | Krezanoski et al. ........ 252/106 |
| 4,046,706 A | | 9/1977 | Krezanoski |
| 4,354,952 A | * | 10/1982 | Reidhammer et al. ...... 252/106 |
| 4,409,205 A | | 10/1983 | Shively |
| 4,440,662 A | | 4/1984 | Tsuzuki et al. |
| 4,613,380 A | | 9/1986 | Chen |
| 4,814,109 A | | 3/1989 | Wittpenn et al. |
| 4,820,352 A | | 4/1989 | Riedhammer et al. |
| 5,209,865 A | | 5/1993 | Wointerton et al. |
| 5,256,420 A | | 10/1993 | Tsao et al. |
| 5,322,667 A | * | 6/1994 | Sherman ...................... 422/28 |
| 5,785,767 A | | 7/1998 | Kimura et al. |
| 5,888,950 A | | 3/1999 | Potini et al. |
| 6,037,328 A | | 3/2000 | Hu et al. |
| 6,096,138 A | * | 8/2000 | Heiler et al. .................. 134/42 |

FOREIGN PATENT DOCUMENTS

| EP | 0 439 429 A2 | 7/1991 | |
|---|---|---|---|
| WO | WO 98/55155 | 12/1998 | |
| WO | 98/55155 | * 12/1998 | |

OTHER PUBLICATIONS

PCT Search Report PCT/US 01/44022 dated Jul. 12, 2002.

* cited by examiner

*Primary Examiner*—Charles Boyer

(57) ABSTRACT

The invention provides a packaging solution for use with hydrophobic contact lenses. The packaging solution of the invention substantially prevents adherence of the lenses to the packages' surfaces, thus preventing deformation or breakage of the lens.

24 Claims, No Drawings

CONTACT LENS PACKAGING SOLUTIONS

FIELD OF THE INVENTION

This invention relates to packaging solutions for use with contact lenses. In particular, the invention provides packaging solutions for use with contact lenses made of hydrophobic materials.

BACKGROUND OF THE INVENTION

The use of contact lenses for correction of ocular refractive disorders is widespread due, in part, to the cosmetic appeal of contact lenses. Preferably, contact lenses are made of materials with high oxygen permeabilities, or oxygen permeabilities of about 10 Dk or greater. However, as a material's oxygen permeability increases, typically the material becomes increasingly hydrophobic.

When a contact lens made of a hydrophobic material comes in contact with another hydrophobic material, the lens' surface adheres to the material's surface. This is problematic in the packaging of the lenses because typical contact lens packaging materials are hydrophobic. Thus, the contact lens can adhere to the packaging material causing lens deformation or breakage.

DESCRIPTION OF THE INVENTION AND PREFERRED EMBODIMENTS

The invention provides a packaging solution for contact lenses made of hydrophobic materials. In particular, the invention provides a packaging solution for contact lenses made of hydrophobic materials that substantially prevents adherence of the lenses to a package's surfaces.

In one embodiment, the invention provides a contact lens packaging solution comprising, consisting essentially of, and consisting of between about 0.1 and about 250 ppm of a surfactant, preferably 0.1 to about 40 ppm more preferably about 1 to about 40 ppm, wherein the surfactant has ahydrophile-lipophile balance of about 10 to about 30. It is an unexpected discovery of the invention that the use of very small amounts of certain surfactants in a lens packaging solution substantially prevents adherence of the hydrophobic lens to a package surfaces substantially eliminating breakage or deformation of the lens in the package.

For purposes of the invention, by "hydrophobic lens" is a lens made from at least one hydrophobic monomer. The packaging solutions of the invention may find particular utility when used for the storage of non-ionic lenses. Lenses for use with the solutions of the invention may be made from acquafilcon, alphafilcon, atlafilcon, etafilcon, bulifilcon, lenefilcon, lidifilcon, lotrafilcon, methafilcon, ocufilcon, perfilcon, phemfilcon, vilifilcon, Saufon, Hydron, and the like, and combinations thereof. Preferably, the lens is an acquafilcon or lenefilcon lens.

The surfactants suitable for use in the invention are of any suitable molecular weight, preferably about 200 to about 1,000,000, more preferably about 10,000 to about 18,000, most preferably about 12,000 to about 18,000. Useful surfactants have a hydrophile-lipophile balance ("HLB") of about 10 to about 30, preferably about 15 to about 25, more preferably about 18 to about 23.

Any of the known surfactants fitting the aforementioned criteria may be used in the solution of the invention provided that the surfactant is compatible, in terms of solubility, in the solution with which it is used. Thus, suitable surfactants include, without limitation, cationic, ionic, non-ionic surfactants, and combinations thereof However, the use of a lens packaging solution containing cationic and ionic surfactants may cause eye irritation. Therefore, preferably the surfactant is a non-ionic surfactant.

Suitable non-ionic surfactants for use in the invention include, without limitation, polyethylene glycol esters of fatty acids, such as polysorbate 20, 60 or 80, all available as TWEEN® surfactants, alkanolamides, amine oxides, ethoxylated alcohols and acids, and surfactants having one or more poly(oxyalkylene) chains, such as poloxamine or poloxamer surfactants, and the like, and combinations thereof Preferably, the surfactant is a polysorbate or poloxamer surfactant. Poloxamer surfactants are commercially available under the name PLURONIC200 that are polyoxyethylene—polyoxypropylene non-ionic surfactants having polyoxyethyl hydrophilic group ends that make up about 10 to about 80 percent by weight of the molecule. Although any of the PLURONIC® surfactants are preferred, particularly preferred for use in the invention is PLURONIC® 127, which is about 70 percent by weight ethylene oxide and has a molecular weight of about 12,000 to about 15,0000.

The surfactant may be combined with any known active and carrier components useful for lens packaging solution. Suitable active ingredients for lens packaging solutions include, without limitation, antibacterial agents, anti-dryness agents, such as polyvinyl alcohol, polyvinylpyrrolidone, and dextran, tonicity agents, and the like, and combinations thereof The packaging solution may be any water-based solution that is used for the storage of contact lenses. Typical solutions include, without limitation, saline solutions, other buffered solutions, and deionized water. The preferred aqueous solution is saline solution containing salts including, without limitation, sodium chloride, sodium borate, sodium phosphate, sodium hydrogenphosphate, sodium dihydrogenphosphate, or the corresponding potassium salts of the same. These ingredients are generally combined to form buffered solutions that include an acid and its conjugate base, so that addition of acids and bases cause only a relatively small change in pH. The buffered solutions may additionally include 2-(N-morpholino)ethanesulfonic acid (MES), sodium hydroxide, 2,2-bis(hydroxymethyl)-2,2',2"-nitrilotriethanol, n-tris(hydroxymethyl)methyl-2-aminoethanesulfonic acid, citric acid, sodium citrate, sodium carbonate, sodium bicarbonate, acetic acid, sodium acetate, and the like and combinations thereof. Preferably, the solution is a borate buffered or phosphate buffered saline solution.

To form the packaging solution, the surfactant along with any additional ingredients are combined with the water-based solution, stirred, and dissolved. The pH of the solution preferably is adjusted to about 6.2 to about 7.5. The lens to be stored in the packaging solution of the invention is immersed in the solution and the solution and lens placed in the package in which the lens is to be stored. Alternatively, the solution may be placed into the package and the lens then placed into the solution. Typically, the package is then sealed by any convenient method, such as by heat sealing, and undergoes a suitable sterilization procedure.

What is claimed is:

1. An article comprising a sterile lens package comprising, within said package, a hydrophobic lens immersed contact lens packaging solution comprising about 0.1 and about 40 ppm of a surfactant selected from the group consisting of a polyethylene glycol ester of a fatty acid, an alkanolamide, an amine oxide, an ethoxylated alcohol, and ethoxylated acid, and combinations thereof, wherein the surfactant has a hydrophile-lipophile balance of about 10 to about 30.

2. The article of claim 1, wherein the surfactant is a polyethylene glycol ester of a fatty acid.

3. The article of claim 1, wherein the surfactant is a polysorbate.

4. The article of claim 1, wherein the packaging solution comprising about 0.1 to about 40 ppm of a surfactant having one or more poly(oxyalkylene) chains, wherein the surfactant has a hydrophile-lipophile balance of about 10 to about 30.

5. The article of claim 4, wherein the surfactant is a poloxamine surfactant, a polaxamer surfactant, or a combination thereof.

6. The article of claim 4, wherein the surfactant is a poloxamer surfactant.

7. The article of claim 6, wherein the poloxamer surfactant is polyoxyethylene-poloxypropylene non-ionic surfactant having polyoxyethyl hydrophilic group ends that make up about 10 to about 80 percent by weight of the molecule.

8. The article of claim 7, wherein the non-ionic surfactant is about 70 percent by weight ethylene oxide and has a molecular weight of about 12,000 to about 15,0000.

9. A method comprising the steps of immersing a hydrophobic contact lens in a packaging solution comprising about 0.1 and about 40 ppm of a surfactant selected from the group consisting of a polyethylene glycol ester of a fatty acid, an alkanolamide, an amine oxide, an ethoxylated alcohol, and ethoxylated acid, and combinations thereof, wherein the surfactant has a hydrophile-lipophile balance of about 10 to about 30; placing said lens and solution into a lens package; and sealing and sterilizing said package.

10. The method of claim 9, wherein the surfactant is a polyethylene glycol ester of a fatty acid.

11. The method of claim 10, wherein the surfactant is a polysorbate.

12. The method of claim 9, comprising the step of immersing the lens for storage in a packaging solution comprising about 0.1 to about 40 ppm of a surfactant having one or more poly(oxyalkylene) chains, wherein the surfactant has a hydrophile-lipophile balance of about 10 to about 30.

13. The method of claim 12, wherein the surfactant is a poloxamine surfactant, a poloxamer surfactant, or a combination thereof.

14. The method of claim 12, wherein the surfactant is a poloxamer surfactant.

15. The method of claim 14, wherein the poloxamer surfactant is a polyoxyethylene—polyoxypropylene non-ionic surfactant having polyoxyethyl hydrophilic group ends that make up about 10 to about 80 percent by weight of the molecule.

16. The method of claim 15, wherein the surfactant is about 70 percent by weight ethylene oxide and has a molecular weight of about 12,000 to about 15,0000.

17. The package of claim 1 wherein said surfactant is present in an amount between about 1 and about 40 ppm.

18. The package of claim 1 wherein said hydrophile-lipophile balance is between about 15 and about 25.

19. The package of claim 1 wherein said a hydrophile-lipophile balance is between about 18 and about 23.

20. A method comprising the steps of placing, in a lens package, a packaging solution comprising about 0.1 and about 40 ppm of a surfactant selected from, the group consisting of a polyethylene glycol ester of a fatty acid, an alkanolamide, an amine oxide, and ethoxylated alcohol, and ethoxylated acid, and combinations thereof, wherein the surfactant has a hydrophile-lipophile balance of about 10 to about 30; immersing a hydrophobic contact lens in said solution; sealing and sterilizing said package.

21. The method of claim 9 or 20 wherein said surfactant is present in an amount between about 1 and about 40 ppm.

22. The method of claim 9 or 20 wherein said hydrophile-lipophile balance is between about 15 and about 25.

23. The method of claim 9 or 21 wherein said a hydrophile-lipophile balance is between about 18 and about 23.

24. A method for reducing adherence of a contact lens comprising hydrophobic materials to a surface of a sterile lens package which contains said contact lens and a packing solution, said method comprising the step of incorporating at least 0.1 and about 40 ppm of a surfactant selected from the group consisting of a polyethylene glycol ester of a fatty acid, an alkanolamide, an amine oxide, and ethoxylated alcohol, and ethoxylated acid, and combinations thereof, wherein the surfactant has a hydrophile-lipophile balance of about 10 to about 30 into said packing solution.

* * * * *